United States Patent
Jiang et al.

(10) Patent No.: US 9,222,945 B2
(45) Date of Patent: *Dec. 29, 2015

(54) METHOD AND KIT FOR THE CLASSIFICATION AND PROGNOSIS OF WOUNDS

(75) Inventors: Wenguo Jiang, Cardiff (GB); Keith Gordon Harding, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 895 days.

This patent is subject to a terminal disclaimer.

(21) Appl. No.: 13/395,572

(22) PCT Filed: Sep. 8, 2010

(86) PCT No.: PCT/GB2010/001696
§ 371 (c)(1),
(2), (4) Date: Mar. 12, 2012

(87) PCT Pub. No.: WO2011/033249
PCT Pub. Date: Mar. 24, 2011

(65) Prior Publication Data
US 2012/0172250 A1    Jul. 5, 2012
US 2013/0116134 A2    May 9, 2013

(30) Foreign Application Priority Data
Sep. 15, 2009  (GB) .................................. 0916124.1

(51) Int. Cl.
C12Q 1/68    (2006.01)
G01N 33/68    (2006.01)

(52) U.S. Cl.
CPC .............. *G01N 33/6893* (2013.01); *C12Q 1/68* (2013.01); *G01N 2800/042* (2013.01); *G01N 2800/20* (2013.01)

(58) Field of Classification Search
None
See application file for complete search history.

(56) References Cited

U.S. PATENT DOCUMENTS

2005/0170445 A1    8/2005    Reichert et al.
2006/0275770 A1    12/2006    Bednarik

FOREIGN PATENT DOCUMENTS

| CN | 101671729 A | 3/2010 |
|---|---|---|
| WO | 9634117 A1 | 10/1996 |
| WO | 0162276 A1 | 8/2001 |
| WO | 03075949 A1 | 9/2003 |
| WO | 2004005312 A1 | 1/2004 |
| WO | 2004050894 A2 | 6/2004 |
| WO | 2004070002 A2 | 8/2004 |
| WO | 2005028681 A1 | 3/2005 |
| WO | 2006053162 A1 | 5/2006 |
| WO | 2006108225 A1 | 10/2006 |
| WO | 2007130423 A2 | 11/2007 |
| WO | 2009076229 A2 | 6/2009 |
| WO | 2010065995 A1 | 6/2010 |
| WO | 2010085606 A1 | 7/2010 |
| WO | 2011033249 A1 | 3/2011 |

OTHER PUBLICATIONS

Affymetrix. Human Genome U133A Array Annotation data, 2009.
Affymetrix. Human Genome U133B Array Annotation data, 2009.
Almeida, et al.; "Randomized, double-blind study of stibogluconate plus human granulocyte macrophage colony-stimulating factor versus stiboglucoate alone in the treatment of cutaneous Leishmaniasis"; The Journal of Infectious Diseases, vol. 180, No. 5, pp. 1735-1737 (Oct. 8, 1999).
Burchert, et al.; "CD82 (KAI1), a member of the tetrasoan family, is expressed on early haemopoietic progenitor cells and up-regulated in distinct human leukaemias", Bri. J Haematology, 107:494-504 (1999).
Cooper et al.; "Wound healing and inflammation genes revealed by array analysis of macrophageless\ PU.I null mice", Genome Biol., 6:R5.1-R5.10 (2004).
Derrick, et al.; "Comparitive analysis of global gene expression profiles between diabetic rat wounds treated with vacuum-assisted closure therapy, moist wound healing or gauze under suction"; International Wound Journal, vol. 5, No. 5, pp. 615-624, (Dec. 2008).
GeneCards® CAR1; http://www.genecards.org/index.php?path=/Search/keyword/carl, accessed on Jun. 10, 2013.
Martinez, et al.; "Treatment of Cutaneous Leishmaniasis with Allopurinol and Stibogluconate"; Clinical Infectious Diseases, vol. 24, No. 2, pp. 165-169 (Feb. 1, 1997).
Moseley et al.; "Extracellular matrix metabolites as potential biomarkers of disease activity in wound fluid: lessons learned from other inflammatory diseases?"; British Journal of Dermatology vol. 150, No. 3, pp. 401-413 (Mar. 1, 2004).
Solomon et al.; "Treatment of cutaneous leishmaniasis with intralesional sodium stibogluconate"; Journal of the European Academy of Dermatology and Venereology, vol. 23, No. 10, pp. 1189-1192, (Oct. 1, 2009).
Vandesompele et al.; "Accurate normalization of real-time quantitative RT-PCR data by geometric averging of multiple internal control genes"; Genome Biology 2002; 3(7):0034.1-0034.11.
Xu, et al.; "Receptor-type Protein-tyrosine Phosphatase-k Regulates Epidermal Growth Factor Receptor Function"; Journal of Biological Chemistry, vol. 280, No. 52, pp. 42694-42700 (Jan. 1, 2005).
International Search Report and Written Opinion for International Application No. PCT/GB2010/001696 dated Nov. 5, 2010.
International Search Report and Written Opinion for International Application No. PCT/GB2010/050362 dated May 24, 2012.

*Primary Examiner* — Jim Ketter
(74) *Attorney, Agent, or Firm* — King & Schickli, PLLC

(57) ABSTRACT

The invention relates to a method and kit for identifying chronic or acute mammalian wound tissue or for determining the prognosis of mammalian wound tissue based upon the identification of at least one key set of molecular markers or genes whose expression pattern is indicative of a given wound type and so representative of a given prognosis.

23 Claims, 3 Drawing Sheets

(56) References Cited

OTHER PUBLICATIONS

Figure 1:
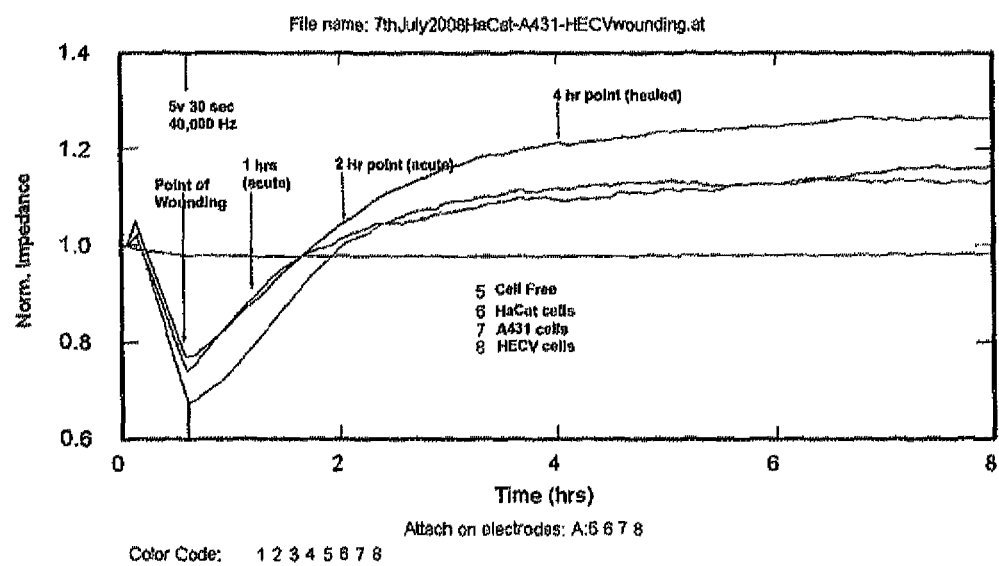

Search Report for British Application No. GB1103898.1 dated Jul. 7, 2011.

Wang, et al.; "Transforming Growth Factor β (TGF-β)-Smad Target Gene Protein Tyrosine Phosphatase Receptor Type Kappa is Required for TGF-β Function"; Moleclar and Cellular Biology, Jun. 2005, vol. 25, No. 11, pp. 4703-4715.

Hardiman, et al.; "Microarray platforms—comparisons and contrasts"; Pharmacogenomics (2004), vol. 5, No. 5, pp. 487-502.

Final Office Action for U.S. Appl. No. 13/326,153 dated Mar. 7, 2014.

Machine Translation of CN 101671729; obtained Feb. 4, 2014; pp. 1-7.

SEQUENCE LISTING

<160> NUMBER OF SEQ ID NOS: 50

<210> SEQ ID NO 1
<211> LENGTH: 20
<212> TYPE: DNA
<213> ORGANISM: Homo sapiens

<400> SEQUENCE: 1
attgagcaag agcagaaact                                              20

<210> SEQ ID NO 2
<211> LENGTH: 38
<212> TYPE: DNA
<213> ORGANISM: Homo sapiens

<400> SEQUENCE: 2
actgaacctg accgtacatt ctggtgcttc aaatctct                          38

<210> SEQ ID NO 3
<211> LENGTH: 20
<212> TYPE: DNA
<213> ORGANISM: Homo sapiens

<400> SEQUENCE: 3
agatgaagaa tggcaaagaa                                              20

<210> SEQ ID NO 4
<211> LENGTH: 37
<212> TYPE: DNA
<213> ORGANISM: Homo sapiens

<400> SEQUENCE: 4
actgaacctg accgtacaat ctgctgttca gatcgtt                           37

<210> SEQ ID NO 5
<211> LENGTH: 20
<212> TYPE: DNA
<213> ORGANISM: Homo sapiens

<400> SEQUENCE: 5
catctcaccc tggagatacc                                              20

<210> SEQ ID NO 6
<211> LENGTH: 36
<212> TYPE: DNA
<213> ORGANISM: Homo sapiens

<400> SEQUENCE: 6
actgaacctg accgtacaca tcgatacagc ctctgc                            36

<210> SEQ ID NO 7
<211> LENGTH: 20
<212> TYPE: DNA

```
<213> ORGANISM: Homo sapiens

<400> SEQUENCE: 7
gctgctgcac attataacac                                              20

<210> SEQ ID NO 8
<211> LENGTH: 38
<212> TYPE: DNA
<213> ORGANISM: Homo sapiens

<400> SEQUENCE: 8
actgaacctg accgtacaaa ctccttcccc acatctat                          38

<210> SEQ ID NO 9
<211> LENGTH: 20
<212> TYPE: DNA
<213> ORGANISM: Homo sapiens

<400> SEQUENCE: 9
agggattttc tcagtccttc                                              20

<210> SEQ ID NO 10
<211> LENGTH: 38
<212> TYPE: DNA
<213> ORGANISM: Homo sapiens

<400> SEQUENCE: 10
actgaacctg accgtacaca tgccctcatc taatgtct                          38

<210> SEQ ID NO 11
<211> LENGTH: 18
<212> TYPE: DNA
<213> ORGANISM: Homo sapiens

<400> SEQUENCE: 11
catccaccca gtgccaac                                                18

<210> SEQ ID NO 12
<211> LENGTH: 36
<212> TYPE: DNA
<213> ORGANISM: Homo sapiens

<400> SEQUENCE: 12 actgaac ctgaccgtac accacacagt cagccacag                            36

<210> SEQ ID NO 13
<211> LENGTH: 20
<212> TYPE: DNA
<213> ORGANISM: Homo sapiens

<400> SEQUENCE: 13
aaatgttgtc acaccaacaa                                              20

<210> SEQ ID NO 14
<211> LENGTH: 38
<212> TYPE: DNA
<213> ORGANISM: Homo sapiens

<400> SEQUENCE: 14
actgaacctg accgtacaag ctgttgacat cagagaca                          38

<210> SEQ ID NO 15
<211> LENGTH: 20
```

<212> TYPE: DNA
<213> ORGANISM: Homo sapiens

<400> SEQUENCE: 15
agatgactga caggttcagc                                         20

<210> SEQ ID NO 16
<211> LENGTH: 38
<212> TYPE: DNA
<213> ORGANISM: Homo sapiens

<400> SEQUENCE: 16
actgaacctg accgtacaga atcgatctca ctttggag                     38

<210> SEQ ID NO 17
<211> LENGTH: 20
<212> TYPE: DNA
<213> ORGANISM: Homo sapiens

<400> SEQUENCE: 17
cagctgacta cccaactctg                                         20

<210> SEQ ID NO 18
<211> LENGTH: 36
<212> TYPE: DNA
<213> ORGANISM: Homo sapiens

<400> SEQUENCE: 18
actgaacctg accgtacaat ctgcaccagt gaaagg                       36

<210> SEQ ID NO 19
<211> LENGTH: 21
<212> TYPE: DNA
<213> ORGANISM: Homo sapiens

<400> SEQUENCE: 19
tcaaattcat atgtctcagc a                                       21

<210> SEQ ID NO 20
<211> LENGTH: 36
<212> TYPE: DNA
<213> ORGANISM: Homo sapiens

<400> SEQUENCE: 20
actgaacctg accgtacagt tgcccatgtc ctcata                       36

<210> SEQ ID NO 21
<211> LENGTH: 18
<212> TYPE: DNA
<213> ORGANISM: Homo sapiens

<400> SEQUENCE: 21
ttcctggacc acaacatc                                           18

<210> SEQ ID NO 22
<211> LENGTH: 38
<212> TYPE: DNA
<213> ORGANISM: Homo sapiens

<400> SEQUENCE: 22
actgaacctg accgtacaca ccgagtcgta cactttgc                     38

<210> SEQ ID NO 23

```
<211> LENGTH: 20
<212> TYPE: DNA
<213> ORGANISM: Homo sapiens

<400> SEQUENCE: 23
cttgattggc agtatggagt                                                    20

<210> SEQ ID NO 24
<211> LENGTH: 37
<212> TYPE: DNA
<213> ORGANISM: Homo sapiens

<400> SEQUENCE: 24
actgaacctg accgtacagt ctaccgcctt gagaaag                                 37

<210> SEQ ID NO 25
<211> LENGTH: 20
<212> TYPE: DNA
<213> ORGANISM: Homo sapiens

<400> SEQUENCE: 25
tatggctgta cctccattgt                                                    20

<210> SEQ ID NO 26
<211> LENGTH: 38
<212> TYPE: DNA
<213> ORGANISM: Homo sapiens

<400> SEQUENCE: 26
actgaacctg accgtacaat atcgtagcat cccttcct                                38

<210> SEQ ID NO 27
<211> LENGTH: 18
<212> TYPE: DNA
<213> ORGANISM: Homo sapiens

<400> SEQUENCE: 27
gtgaagccct tgaccagt                                                      18

<210> SEQ ID NO 28
<211> LENGTH: 38
<212> TYPE: DNA
<213> ORGANISM: Homo sapiens

<400> SEQUENCE: 28
actgaacctg accgtacatt ggtatagtcc tcggtttg                                38

<210> SEQ ID NO 29
<211> LENGTH: 19
<212> TYPE: DNA
<213> ORGANISM: Homo sapiens

<400> SEQUENCE: 29
ggtgctactc ctctgcatt                                                     19

<210> SEQ ID NO 30
<211> LENGTH: 37
<212> TYPE: DNA
<213> ORGANISM: Homo sapiens

<400> SEQUENCE: 30
actgaacctg accgtacaag aaaggatcct cctcctc                                 37
```

```
<210> SEQ ID NO 31
<211> LENGTH: 18
<212> TYPE: DNA
<213> ORGANISM: Homo sapiens

<400> SEQUENCE: 31
agtcctcctg gctgacaa                                                 18

<210> SEQ ID NO 32
<211> LENGTH: 36
<212> TYPE: DNA
<213> ORGANISM: Homo sapiens

<400> SEQUENCE: 32
actgaacctg accgtacaca cagcctcatc caacac                             36

<210> SEQ ID NO 33
<211> LENGTH: 20
<212> TYPE: DNA
<213> ORGANISM: Homo sapiens

<400> SEQUENCE: 33
gagctggatg agaacaacac                                               20

<210> SEQ ID NO 34
<211> LENGTH: 38
<212> TYPE: DNA
<213> ORGANISM: Homo sapiens

<400> SEQUENCE: 34
actgaacctg accgtacaaa agaagtggca ggaagagt                           38

<210> SEQ ID NO 35
<211> LENGTH: 20
<212> TYPE: DNA
<213> ORGANISM: Homo sapiens

<400> SEQUENCE: 35
cctacacagc ggtcagatag                                               20

<210> SEQ ID NO 36
<211> LENGTH: 38
<212> TYPE: DNA
<213> ORGANISM: Homo sapiens

<400> SEQUENCE: 36
actgaacctg accgtacaag cagaagtttc tccctctt                           38

<210> SEQ ID NO 37
<211> LENGTH: 20
<212> TYPE: DNA
<213> ORGANISM: Homo sapiens

<400> SEQUENCE: 37
aacttcccca acttccttag                                               20

<210> SEQ ID NO 38
<211> LENGTH: 38
<212> TYPE: DNA
<213> ORGANISM: Homo sapiens

<400> SEQUENCE: 38
actgaacctg accgtacaag caaggacaga aactcaga                           38
```

```
<210> SEQ ID NO 39
<211> LENGTH: 18
<212> TYPE: DNA
<213> ORGANISM: Homo sapiens

<400> SEQUENCE: 39
atgccaggag acgacctc                                                 18

<210> SEQ ID NO 40
<211> LENGTH: 38
<212> TYPE: DNA
<213> ORGANISM: Homo sapiens

<400> SEQUENCE: 40
actgaacctg accgtacaga tcttacgctt cccttacc                           38

<210> SEQ ID NO 41
<211> LENGTH: 17
<212> TYPE: DNA
<213> ORGANISM: Homo sapiens

<400> SEQUENCE: 41
gtctcgttca agctggg                                                  17

<210> SEQ ID NO 42
<211> LENGTH: 36
<212> TYPE: DNA
<213> ORGANISM: Homo sapiens

<400> SEQUENCE: 42
actgaacctg accgtacagg ttgccgtgtc ctcctc                             36

<210> SEQ ID NO 43
<211> LENGTH: 20
<212> TYPE: DNA
<213> ORGANISM: Homo sapiens

<400> SEQUENCE: 43
agtgactggg gatagtgaag                                               20

<210> SEQ ID NO 44
<211> LENGTH: 38
<212> TYPE: DNA
<213> ORGANISM: Homo sapiens

<400> SEQUENCE: 44
actgaacctg accgtacaca gagcacaact gttcctTt                           38

<210> SEQ ID NO 45
<211> LENGTH: 40
<212> TYPE: DNA
<213> ORGANISM: Homo sapiens

<400> SEQUENCE: 45
cattcgagac tacaacagca ctgtactttg ctttcctgct                         40

<210> SEQ ID NO 46
<211> LENGTH: 20
<212> TYPE: DNA
<213> ORGANISM: Homo sapiens

<400> SEQUENCE: 46
ctgtagtctt cggaatggac                                               20
```

```
<210> SEQ ID NO 47
<211> LENGTH: 20
<212> TYPE: DNA
<213> ORGANISM: Homo sapiens

<400> SEQUENCE: 47
atggatctga agaaattgga                                              20

<210> SEQ ID NO 48
<211> LENGTH: 38
<212> TYPE: DNA
<213> ORGANISM: Homo sapiens

<400> SEQUENCE: 48
actgaacctg accgtacaag acaatttttg ccactcat                          38

<210> SEQ ID NO 49
<211> LENGTH: 20
<212> TYPE: DNA
<213> ORGANISM: Homo sapiens

<400> SEQUENCE: 49
ggggactatg aggagatgat                                              20

<210> SEQ ID NO 50
<211> LENGTH: 38
<212> TYPE: DNA
<213> ORGANISM: Homo sapiens

<400> SEQUENCE: 50
actgaacctg accgtacagt ggaggtcttg atgtgaat                          38
```

METHOD AND KIT FOR THE CLASSIFICATION AND PROGNOSIS OF WOUNDS

CROSS REFERENCE TO RELATED APPLICATIONS

This application is a filing under 35 U.S.C. §371 of PCT/GB2010/001696 filed with the Patent Cooperation Treaty on Sep. 8, 2010, which claims priority to and benefit of Great Britain Patent Application No. GB 0916124.1, filed Sep. 15, 2009, all of which are herein incorporated in their entirety by reference.

REFERENCE TO SEQUENCE LISTING

The Sequence Listing submitted Mar. 12, 2012, as a text file named "UCC_0029P_ST25.txt," created on Mar. 9, 2012, and having a size of 6.88 Kilo bytes is hereby incorporated by reference.

FIELD OF THE INVENTION

The present invention relates to a method and kit, including parts thereof, for the classification and prognosis of mammalian and, in particular, human wounds. More specifically, the method involves identifying one or more gene expression patterns that enables one to distinguish between 'abnormal or non-healing' chronic wounds or 'normally healing' acute wounds. Advantageously, the said gene expression pattern(s) allow(s) informed decision making in the selection of treatment and the prediction of outcome following use of a given therapy. Further the invention identifies new targets for use in wound therapy.

BACKGROUND OF THE INVENTION

In one form or another, non-healing or chronic i.e. poorly healing wounds constitute a major burden on the UK health system. Moreover, in certain member countries of the EU health expenses relating to wound healing are already approaching the third most expensive drain on health care funding.

Chronic foot ulcers are a major complication of diabetes, accounting for up to 25% of all hospital admissions involving diabetes, and at a cost to the UK National Health Service of £250M annually. Chronic foot ulcers cause substantial morbidity, impair the quality of life, and are the major cause of lower limb amputation. Despite careful attention to foot care, as many as 25% of diabetics develop foot ulcers in their lifetimes. The causes of lower limb ulceration are the same in diabetics as in non-diabetics, namely neuropathy, ischaemia and trauma. Moreover, this "pathogenic triad" predisposes wounds to infection, which can also contribute to the non-healing nature of the wounds.

Current treatment involves removing pressure from the area, debridement, wound dressing and management of infection: surgical resection and vascular reconstruction may be required in more advanced disease which, ultimately, may necessitate amputation.

In addition to lower limb ulcers in diabetics, another major resource health cost is created by pressure wounds or ulcers that result, for example, from failure to provide routine nursing or medical care. In the UK 412,000 people are affected annually by this sort of wound at a cost of £1.4-2.1 billion.

The healing of a wound is controlled by complex biological processes that involve a diverse number of cell types; complex interactions between cells and tissues; the activation of the immune system and the activation of the angiogenic process.

A typical healing process can be divided into 5 distinct, but closely related, stages: clotting stage, acute inflammation stage, matrix deposition stage, capillary formation stage and re-epithelialisation stage. A diverse number of factors controls each of these stages. Deficiencies in any aspect of the process may result in defective wound healing. Thus, a 'normal' healing process may be defective as a result of either intrinsic or external factors, which manifest as 'abnormal or non-healing' i.e. chronic wounds. It is these 'non-healing' or chronic wounds that present the greatest challenge to the quality of a patient's life and mounting expenses to the healthcare system.

Although some common clinical/pathological factors may assist in pre judging if a wound may be 'healing' or 'non-healing', or if an acute wound may become chronic, there is no specific laboratory test(s) to distinguish wound type. Additionally, there is no clear way to define how to predict the healing process and a patient's likely response to treatment in wound care.

We have therefore developed a method for determining the prognosis of a given wound which is relatively straightforward to perform, efficient to undertake and provides an accurate indication of the likely outcome, before or during treatment, of a wound. Our method uses a small but highly representative sample of markers which distinguishes between acute wounds and chronic wounds and is therefore particularly relevant in the selection of treatment for a given wound and particularly accurate in determining the likely outcome, following treatment, of a given wound.

In summary, we have identified a plurality of molecular markers that have relevance in determining the prognosis of a given wound. Collectively these markers constitute at least one molecular signature and the expression of these markers in wound tissue from a patient constitutes a gene expression pattern that is indicative of a given wound type and prognosis. In addition to this, we have analysed the said molecular signature in order to identify which markers are the best indicators of wound type and prognosis, in other words those that contribute most to the predictive ability of the molecular signature. This subset of markers is known, collectively, as the refined molecular signature and the expression of these markers constitutes a refined gene expression pattern.

Reference herein to the term marker is reference to one named gene whose full identity is available on the www.NCBI.LM.NIH.gov database via its accession details, or is well known to those skilled in the art, please see Appendix-1. Moreover, a collection of these markers, or molecular signature, is to be construed accordingly.

The elucidation of the molecular signatures described herein has involved the systematic and careful examination of, in the first instance, 34 samples of wound tissue and 110 genetic molecular markers and, in the second instance, validation studies involving 71 samples of wound tissue and investigations to identify the use of the markers described herein.

However, having completed this arduous task we have, surprisingly, found that, in fact, very few genes need to be examined in order to provide an accurate classification and prognosis for a given sample of wound tissue. Even more surprisingly, we have been able to further reduce this number by identifying those molecular markers that contribute most to the predictive ability of our molecular signature, so for example, only 25 or, more ideally, 14 genes need to be examined. This means that our methodology has immediate application and can be performed quickly and routinely in a clinical context. In fact, we suggest that our methodology forms part of the standard treatment regime of wound care so that the relevant clinician can, at an early stage, determine the classification and outcome of a particular wound and so match the treatment accordingly. Thus, for example, in the case of an individual who presents with a signature indicative of an 'abnormal' or chronic wound a thorough and aggressive form of therapy might be prescribed. Conversely, if an individual has a signature indicative of a 'normally healing' or acute wound, the clinician can prescribe a less aggressive treatment, thereby saving the patient from any unnecessary distress and unwanted side effects and also saving the NHS from any costly and unnecessary, intervention. Our method therefore not only serves to ensure that individuals receive treatment tailored to their wound status, but it can improve the quality of a patient's life during treatment, by ensuring that aggressive therapy is only prescribed in those cases where it is necessary.

STATEMENTS OF INVENTION

Accordingly, in one aspect of the invention there is provided a method for identifying chronic mammalian wound tissue or for determining the prognosis of mammalian wound tissue, which method comprises:

(a) examining a sample of wound tissue from an individual in order to determine the levels of expression of genes encoding the molecular markers shown in Table 2, and;

(b) where the following genes show decreased expression: ARP2, CREB1l, VEGF-C, IL8RB, IL17BR, Claudin-5, CAR1 and Endomuscin-2, and;

(c) where the following gene shows normal expression: TEM4 and;

(d) where the following genes show increased expression: Psoriasin, IL22R, KAI1, PTPRK, and TEM7R, (e) concluding that the individual from whom the tissue sample has been taken has a chronic wound.

In yet a further preferred method of the invention additional studies are undertaken to determine whether any one or more of the following markers show a decreased level of expression:

VEGF-D, IL17C, β-Catenin, RON, BMP15, PEDF, RhoGDI-G and N-WASP and/or;

any one or more of the following markers show a normal level of expression:

WAVE2, AMFR, PAR4;

and, where this is the case, concluding that the individual from whom the tissue sample has been taken has a chronic wound.

In a second independent aspect of the invention there is provided a method for identifying acute mammalian wound tissue or for determining the prognosis of mammalian wound tissue, which method comprises:

(a) examining a sample of wound tissue from an individual in order to determine the levels of expression of genes encoding the molecular markers in Table 2, and;

(b) where the following genes show increased expression: ARP2, CREB1l, Psoriasin, IL22R, TEM4, IL8RB, IL17BR, Claudin-5, KAI1, PTPRK, CAR1 and TEM7R; and (c) concluding that the individual from whom the tissue sample has been taken has an acute wound.

In yet a further preferred method of the invention additional studies are undertaken to determine whether either of the following markers shows normal expression VEGF-C and Endomuscin-2 and, where this is the case, concluding that the individual from whom the sample has been taken has an acute wound.

In yet a further preferred method of the invention additional studies are undertaken to determine whether any one or more of the following markers show an increased level of expression:

VEGF-D, IL17C, RON, WAVE2, N-WASP and AMFR, PAR4 and/or;

any one or more of the following markers show a normal level of expression:

β-Catenin, BMP15 and/or;

any one or more of the following markers show a decreased level of expression PEDF, RhoGDI-G; and where this is the case, concluding that the individual from whom the tissue sample has been taken has an acute wound.

In the above methods of the invention said first and second aspects may be undertaken on a selected sample of wound tissue either simultaneously or sequentially and, when the said methods are undertaken sequentially the skilled worker may choose whether the method pertaining to the first aspect of the invention is undertaken before or after the method pertaining to the second aspect of the invention and, in any event, the invention described herein is intended to cover any order or combination of said methods.

In each of the above methods of the invention, the assay is, ideally, undertaken using human tissue.

In each of the above methods of the invention, ideally, the sample of tissue that is examined is assayed for the presence of RNA, preferably total RNA and, more preferably still, the amount of mRNA. It will be apparent to those skilled in the art that techniques available for measuring RNA content are well known and, indeed, routinely practiced by those in the clinical diagnostics field. Such techniques may include reverse transcription of RNA to produce cDNA and an optional amplification step followed by the detection of the cDNA or a product thereof.

In an alternative embodiment of the invention the method involves assaying for the protein encoded by each of the said molecular markers and so, typically, but not exclusively, involves the use of agents that bind to the relevant proteins and so identify same. Common agents are antibodies and, most ideally, monoclonal antibodies which, advantageously, have been labelled with a suitable tag whereby the existence of the bound antibody can be determined. Assay techniques for identifying proteins are well known to those skilled in the art and, indeed, used every day by workers in the field of clinical diagnostics. Such assay techniques may be applied by the skilled worker to utilise the invention.

In further preferred methods of working the invention the level of expression of a given molecular marker is determined having regard to a reference gene (such as, but not limited to, GAPDH) within a control sample, wherein the control sample is a sample of normal tissue, ideally normal skin tissue, more ideally still, normal tissue taken from the same limb or region as the wound tissue to be assayed and, further, from the same or a different individual as the patient providing the test sample. Thus increased expression refers to an increase in expression of a selected gene having regard to the expression of, for example, GAPDH in the respective tissue. Conversely, decreased expression refers to a decrease in expression of a selected gene having regard to, for example, GAPDH expression in the respective tissue. Alternatively, the level of expression of a given molecular marker is determined having regard to a reference gene, wherein the reference gene is the same gene or another selected gene (such as a housekeeping gene) within a control sample, wherein the control sample is a sample of known non-healing chronic wound tissue or known acute wound tissue, ideally from the same limb or region as the wound tissue to be examined and, in this instance, one is looking to see whether the same expression pattern of the selected genes exists as that in the known wound tissue.

Alternatively still, the said control is a recognised standard for expression of each relevant gene in a healthy individual.

Ideally, increased or decreased expression is statistically relevant at the 5% confidence level or less.

In an alternative embodiment of the invention the level of gene expression may be measured by real-time quantitative PCR, using a method disclosed in Jiang et al 2003a and 2004. [Jiang W G, Watkins G, Lane J, Douglas-Jones A, Cunnick G H, Mokbel M, Mansel R E. Prognostic value of Rho family and rho-GDIs in breast cancer. *Clinical Cancer Research,* 2003a, 9, 6432-6440; Jiang W G, Watkins G, Fodstad O, Douglas-Jones A, Mokbel K, Mansel R E. Differential expression of the CCN family members Cyr61 from CTGF and Nov in human breast cancer. *Endocrine Related Cancers,* 2004, 11: 781-791].

According to yet a further aspect of the invention there is provided a kit for performing any one or more of the aforementioned methods wherein said kit comprises:

(a) a plurality of probes limited to those for detecting and quantifying the expression level of all the molecular markers specified in Table 2; and (b) optionally, reagents and instructions pertaining to the use of said probes.

In yet a further preferred aspect of the invention there is provided a kit for determining the prognosis of mammalian wound tissue which comprises:

(a) a plurality of probes limited to those for detecting and quantifying the expression level of at least one transcript or polypeptide/protein of each one of the genes in Table 2, and;

(b) optionally, reagents and instructions pertaining to the use of said probes.

Ideally, the instructions describe how to determine the expression level of each of said genes.

In yet a further embodiment of the invention, said kit additionally comprises:

(a) a plurality of probes limited to those for detecting and quantifying the expression level of at least one further molecular marker specified in Table 1 but not shown in Table 2; and (b) optionally, reagents and instructions pertaining to the use of said probes.

In yet a further embodiment of the invention, said kit additionally comprises:

(a) a plurality of probes limited to those for identifying and quantifying the expression level of at least one transcript or polypeptide/protein of at least one gene shown in Table 1 but not shown in Table 2; and (b) optionally, reagents and instructions pertaining to the use of said probes.

Ideally, the instructions describe how to determine the expression level of each of said genes.

In a further aspect of the invention there is provided a kit comprising or containing any selected combination of the aforementioned sets of probes for identifying the aforementioned sets of molecular markers or genes.

According to a yet further aspect of the invention there is provided a microarray comprising or containing any one or more of the aforementioned sets of probes for identifying the expression of any one or more of the aforementioned molecular markers or genes.

In another aspect of the invention, there is provided a kit for determining wound type in a patient, which kit comprises:

(a) at least one microarray comprising a plurality of probes limited to those for identifying at least one set of the molecular markers described in the above methods; and, optionally, (b) a second microarray comprising a plurality of probes limited to those for identifying the same set of molecular markers in an internal standard that represents the normal level of expression of said markers.

The invention also provides a set of probes as described above.

According to a further aspect of the invention there is provided a method for treating a wound which comprises performing any one or more of the above methods for determining the classification or prognosis of wound tissue in order to identify whether said wound tissue is non-healing chronic wound tissue or acute wound tissue and then selecting an appropriate course of treatment based upon the said classification or prognosis of said tissue.

According to a further aspect of the invention there is provided a collection of target genes, as shown in Table 2, for use in the development of novel wound healing treatments.

Figure 2:
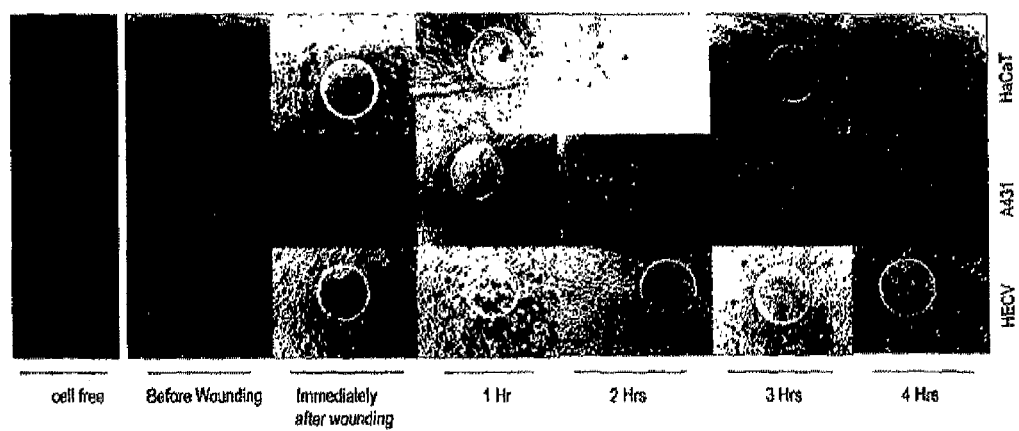
Figure 3:
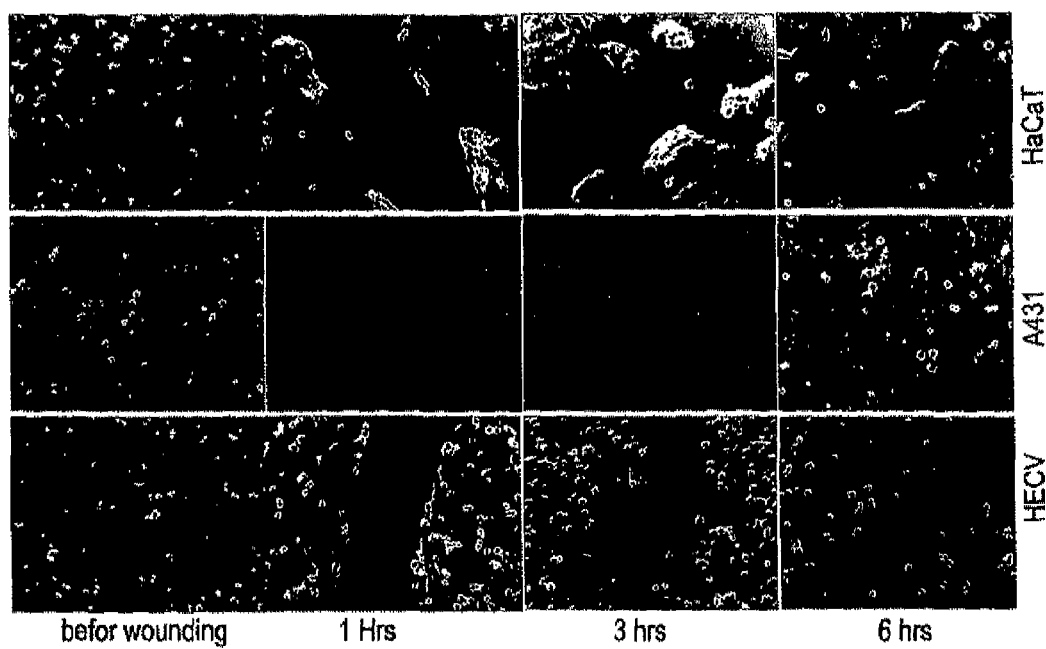

The present invention will now be described by way of the following examples with particular reference to Tables 1-2 and FIGS. 1-3 wherein:

Table 1 shows the 25 genes comprising the molecular signature of the invention;

Table 1b shows the primers used to quantify the expression of the genes shown in Table 1;

Table 2 shows the 14 genes comprising the refined molecular signature of the invention;

Tables 3-12 show the data obtained when using the 25 gene molecular signature or the 14 refined gene molecular signature to classify wound tissue;

FIG. 1 shows monitoring the healing process by electric cell sensing (ECIS). A monolayer of cells in the ECIS chambers were wounded at 5 v 30 sec (indicated). The change of electric impedance was monitored before and after wounding. Three hours after wounding, the migration/healing reached its stable phase;

FIG. 2 shows morphological evaluation of wounding using the ECIS based wounding assay. Confluent cells on electrode were wounded at 6 v for 60 seconds, after which the migration of cells into the wounding space was recorded over a 4 hour period. After 3 hours, the wounds were largely healed; and FIG. 3 shows morphological evaluation of wounding using the scratch wounding assay. Confluent cells on electrode were wounded, after which the migration of cells into the wounding space was recorded over a 6 hour period. After 3 hours, the wounds were largely healed.

MATERIALS AND PROCEDURE

Cells (A431, HECV, MRC5, HaCaT,) were purchased from ATCC, InterLab, ECACC and German Cancer Institute and maintained in tissue culture media supplemented with 10% FCS and antibiotics. Recombinant human HGF was from the applicants' research laboratory. (Metastasis and Angiogenesis Research Group, University Department of Surgery, Cardiff University, Heath Park, Cardiff, CF14 4XN, UK).

Tissues Processing

Tissue preparation and construction of cDNA bank from human wound/skin tissues.

Tissues were frozen sectioned on a cryostat (Leica). A portion of the sections were kept for histological analysis. Approximate 20 sections were pooled and homogenised using a hand-held homogenizer using a procedure to extract RNA from the tissues. See below.

RNA extracted from the tissues was quantified and a cDNA bank was generated from equal amount of RNA.

Expression levels of sets of gene transcripts were analysed on a cohort of samples from patients with acute or chronic wounds as well as normal skin. The tissues and normal skins were collected under an approval from the local ethical committee (Ethical approval ID: 05/WSE03/92). Written informed consent was obtained from each patient who agreed to a biopsy being taken. Chronic wound tissues were from patients with chronic leg ulcers. Acute wound tissues were obtained from patients with acute surgical wounds after undergoing excision of pilonidal disease. Normal tissues were from normal volunteer's normal skin.

Extraction of RNA From Cells and Tissues and cDNA Synthesis

Frozen sections of tissues were cut at a thickness of 5-10 μm and were kept for immunohistochemistry and routine histology (Jiang W G, Watkins G, Lane J, Douglas-Jones A, Cunnick G H, Mokbel M, Mansel R E. Prognostic value of Rho family and rho-GDIs in breast cancer. *Clinical Cancer Research*, 2003a, 9, 6432-6440). A further 15-20 sections were homogenised using a hand-held homogeniser, in ice-cold RNA extraction solution (RNA isolation reagent, ABgene, Surrey, England). The concentration of RNA was determined using a UV spectrophotometer (Jiang W G, Watkins G, Lane J, Douglas-Jones A, Cunnick G H, Mokbel M, Mansel R E. Prognostic value of Rho family and rho-GDIs in breast cancer. *Clinical Cancer Research*, 2003a, 9, 6432-6440). Reverse transcription was carried using a RT kit with an anchored oligo-dt primer supplied by AbGene™, using 1 μg total RNA in 96-well plate. The quality of cDNA was verified using β-actin primers. RNA extraction kit and RT kit were obtained from AbGene Ltd, Surrey, England, UK. PCR primers (see Table 1b) were designed using Beacon Designer (California, USA) and synthesised by Invitrogen™ Ltd (Paisley, Scotland, UK). Molecular biology grade agarose and DNA ladder were from Invitrogen. Mastermix for routine PCR and quantitative PCR was from AbGene.

Quantitative Analysis of Genetic Markers

The transcript level of the said genes (Tables 1 and 2) from the above-prepared cDNA was determined using a real-time quantitative PCR, based on the Amplifuor™ technology (Nazarenko I A, Bhatnagar S K, Hohman R J. *A closed tube format for amplification and detection of DNA based on energy transfer*. Nucleic Acids Res. 1997 Jun. 15; 25(12): 2516-21); modified from a method previously reported (Jiang W G, Watkins G, Lane J, Douglas-Jones A, Cunnick G H, Mokbel M, Mansel R E. Prognostic value of Rho family and rho-GDIs in breast cancer. *Clinical Cancer Research*, 2003a, 9, 6432-6440; and Jiang W G, Douglas-Jones A, and Mansel R E. Level of expression of PPAR-gamma and its co-activator (PPAR-GCA) in human breast cancer. *International Journal of Cancer*, 2003b, 106, 752-757). Briefly, a pair of PCR primers (see Table 1b) were designed using the Beacon Designer software (version 2, Biosoft, Palo Alto, Calif., USA). To one of the primers (routinely to the antisense primer in our laboratory), an additional sequence, known as the Z sequence (5' actgaacctgaccgtaca'3) which is complementary to the universal Z probe (Nazarenko et at 1997, as above) (Intergen Inc., England, UK), was added. A Taqman™ detection kit for β-actin was purchased from Perkin-Elmer™.

The reaction was carried out using the following: Hot-start Q-master mix (Abgene), 10 pmol of specific forward primer, 1 pmol reverse primer which has the Z sequence, 10 pmol of FAM-tagged probe (Intergen Inc.), and cDNA from approximate 50 ng RNA (calculated from the starting RNA in the RT reaction). The reaction was carried out using IcyclerIQ™ (Bio-Rad™, Hemel Hamstead, England, UK) which is equipped with an optic unit that allows real time detection of 96 reactions, using the following condition: 94° C. for 12 minutes, 50 cycles of 94° C. for 15 seconds, 55° C. for 40 seconds and 72° C. for 20 seconds (Jiang W G, Douglas-Jones A, and Mansel R E. Level of expression of PPAR-gamma and its co-activator (PPAR-GCA) in human breast cancer. *International Journal of Cancer*, 2003b, 106, 752-757 and Jiang W G, Grimshaw D, Lane J, Martin T A, Parr C, Davies G, Laterra J, and Mansel R E. Retroviral hammerhead transgenes to cMET and HGF/SF inhibited growth of breast tumour, induced by fibroblasts. *Clinical Cancer Research*, 2003c, 9, 4274-4281). The levels of the transcripts were generated from an internal standard (Jiang W G, Watkins G, Lane J, Douglas-Jones A, Cunnick G H, Mokbel M, Mansel R E. Prognostic value of Rho family and rho-GDIs in breast cancer. *Clinical Cancer Research*, 2003a, 9, 6432-6440) that was simultaneously amplified with the samples. The results are shown here in two ways: levels of transcripts based on equal amounts of RNA, or as a target/GAPDH ratio.

Deciphering the Expression Pattern and Deduction of the Molecular Signature

The pattern of expression of the gene transcripts was first analysed against the nature of the samples using Minitab software (Minitab Inc., State College, Pa. 16801, USA). 'refining'—Selection of potential candidates: this is based on a Macro (WD-Sig Macro) written for the study cohort by the Inventors that allows automatic statistical analysis of expression levels in different tissue type within the Minitab application window. 'selection of final list': this is based on the characteristics of a given gene transcript and its ability to discreetly separate the chronic group from other groups. This involved the use of Excel (Microsoft Office 2007 version, used for grouping and calculation of basic statistics), SPSS (SPSS Inc., Chicago, Ill., US, for advanced statistical analysis within the three groupings) and Minitab analysis (for non-parametric Kriskul Wallis test) tool. 'compilation of expression signature'. This is again based on an 'add one and minus one' procedure by using the multiple cells tabulation methods, using a macro written for the study. The macro allows one to automatically and rapidly conduct statistical analysis within Minitab software, after removing candidate genes from the list.

Manufacturing the 'refined' kit. After finalising the gene signature, we manufactured the testing kit, based on the signature, by first making up all the test materials for the test genes and then automatically pipetting into 96 well plates, which were ready for use in testing clinical and cell materials. The kit was made in the laboratory and stored at −20° C. until use.

In Vitro Wound Assays and Validation Studies.

Monitoring the healing process using electric cell sensing (ECIS).

The ECIS 1600R model instrument and 8W10 arrays (Applied Biophysics Inc, NJ, US) were used in the study. After treating the array surface with a Cysteine solution, the arrays were incubated with complete medium for 1 hour. The same number of lung cancer cells, HaCat, A431 and HECV (200,000 per well) were added to each well (cell free was the control). The cells were then immediately subject to wounding using the integrated elevated field module in the instrument in the 1600R model (5 v, 30 seconds for each well). The changes of cellular impedance were immediately recorded after wounding (400, 4000 and 40,000 Hz). The data was analysed using the ECIS RbA modelling software, supplied by the manufacturer. At the respective time point, images from cells were taken to verify the healing status of the cells.

Monitoring the healing process using time-lapsed videography.

In order to ascertain the healing process as seen in ECIS and in a scratch wounding assay, the healing was monitored morphologically using the following two methods on a time lapse video: electric induced wounding and scratch wounding assays. The former was based on the ECIS model, in which a confluent monolayer of cells was electronically wounded and the healing (migration of cells into the wounding space over the electrode) was monitored (before and after wounding). The latter was based on scratching the monolayer of cells using a fine plastic scraper, followed by monitoring. The monitoring lasted for up to 6 hours or until the wound closed.

Validation studies using in vitro cell models.

Human endothelial cells, fibroblasts, melanoma cells, and keratinocytes were used. Cells or cell mixtures were allowed to reach confluence in a 6 well plate. They were then wounded using a plastic scraper. Multiple wounds (20) were created in each well. A wounded cell layer was allow to recover over 1 hour, 2 hours, 4 hours and 7 hours periods, representing the 'acute' (1 and 2 hours) and 'healed' (4 and 7 hours) phases of the study (deduced from, FIG. 1). RNA was extracted and cDNAs were generated as above. The expression profile of the wound signature was tested on these samples.

Statistical Analysis was conducted using Minitab, SPSS and an online Chi-square service tool (http://www.people.ku.edu/~preacher/chisq/chisq.htm).

Part 1

Identification of Wound Signatures 34 human tissues were used, which comprised 14 chronic wound tissues, 10 acute wound tissues and 10 normal skins.

2 sets of gene signature were obtained:

WDsig-1: this has a list of 25 genes that allow evaluation of the fate of a given wound and guidance for treatment (gene list in Table-1).

WDsig-2: this refined molecular signature was deduced from WDsig-1 and has a list of 14 genes which form the final list of the product and allows one to predict the fate of a wound (gene list in Table-2)

Wound Signatures and Healing of Wounds

The refined molecular signature WDsig-2 allows clear distinction of a chronic wound from acute wound and normal skin.

We have used two criteria to distinguish the wounds:

To predict the nature of the wound by distinguishing chronic wounds from acute wounds and normal skin with near 'zero' overlapping a calculation pattern (referred to here as AO>10) was obtained that returns with a Chi-square value of 25.33 ($p=0.00000316$). 100% of chronic wounds were predicted and 90% of acute wounds predicted. (Table-3). To predict the nature of the wound by distinguishing chronic wounds from acute wounds with 'zero' overlapping a calculation pattern (referred to here as AO123d) was obtained that returns with a Chi-square value of 25.868 ($p=0.00000268$). 100% of chronic wounds were predicted and 100% of acute wounds predicted. (Table-4).

In Table 5 we show the data that demonstrates that acute wounds can be clearly distinguished from chronic wounds (Table-5), using the refined molecular signature and the F5>5 format of data analysis. The refined signature provided a clear distinction between the two types of wounds ($p=0.00000676$).

In Tables 6 we show the data that demonstrates that acute wounds can be distinguished from normal skin (Table-6a) and chronic wounds can be distinguished from normal skin (Table-6b). As shown in the respective table, the refined molecular signature also enables one to distinguish between normal skin and acute or chronic wounds, respectively, although the statistical power is weaker for normal/chronic wounds.

Moreover, work using the WDsig-1 also allows a clear distinction between chronic wound, acute wound and normal skin.

We have used two criteria to distinguish the wounds:

To distinguish acute wound from chronic wounds and normal skin we have used a two group fashion (Table-7).

To distinguish chronic wounds from acute wounds and normal skin we have also used a three group fashion (Table-8).

Validation of Signatures Using In Vitro Wound Healing Model.

The validation was first carried out using the ECIS model and wounding assay in order to obtain the best time point(s) for such a study, following which, the analysis was carried out using the manufactured refined molecular signature kit.

In Vitro Wounding Model and Point of Monitoring.

This experiment was to determine the appropriate time points for the 'acute' and 'chronic/healed' phases. Cell monolayer was electrically wounded and the healing process recorded. As shown in FIG. 1, 1-2.5 hours after wounding, the healing process was in its linear phase, thus representing the best time point for a rapid (acute) healing process. After 3 hours, the healing process reached its stable phase, thus representing the 'healed/stable' stage. The unwounded cells; 2 hours; and 4 hours were therefore chosen to represent the three possible stage of healing: unwounded, acute and healed. The electric signal was fully supported by the morphological changes of the cells (FIGS. 2 and 3).

A431 Cell Model.

The wounding and monitoring time points. The initial validation was based on a cell model, which may reflect the healing nature of a human wound: the co-cultured endothelial, fibroblasts and epithelial cells. Here, HECV endothelial cells, MRC5 fibroblasts and A431 melanocytes, in a ratio of 20:10:100, were allowed to reach confluence. The cells were wounded. The recovery allowed for 1 hour, 2 hours and 4 hours. We took the non-wounded monolayer as non-wound, 2 hours after wounding as acute wounding where the repair is at the most active stage, and 4 hours as near complete healing (as the wounds were mostly closed).

The refined molecular signature showed the rapid rise of expression profile during the 'acute' phase. The signature of expression returns to normal 'non-wounded' level. As shown in the following table, the pattern of expression and the power of prediction of the 'in vitro wounding healing' is similar to that seen in human wounds ($p=0.00000374$, Table 9).

HaCat Cell Model.

Similar to the A431 model, a similar pattern was seen with the HaCaT cell model. The keratinocytes migrate at a slower pace. The healing stage was therefore divided into acute (3 hours) and healed (6 hours). The change of gene pattern resulted in a significant difference between the unwounded, acute and healed ($p=0.003887$, Table-10).

Endothelial Cell Model.

Using the endothelial cell wounding model, the change of the refined signature was also found to be highly significant (Table-11).

We further adopted the Endothelial/fibroblast co-culture model by plate HECV and MRC5 cells at a ratio of 5:1. Wounding assay using this cell model showed a similar change of gene expression pattern (Table-12).

Discussion

The present invention has provided a novel tool in order to distinguish between non-healing, chronic or acute wounds. It is believed that this makes it the first such molecular signature derived from a clinical setting. In addition, the validation study using in vitro cell models has shown the validity of the signature in evaluating the healing process.

The biological impact of the signature can be read from the nature of the candidates genes in the signature. The signature list comprises clusters that link to cell migration (ARP2, KAI1, CAR-1), angiogenesis/lymphangiogenesis (VEGF-C, TEM-4, TEM7R), gene transcription regulation (CREB1I), immune functions (IL-8RB, IL-22R, IL17BR), regulation of cellular adhesion behaviours (PTPRK, Claudin-5) and genes that link to skin disorder (Psoriasin). The complexity of the list therefore reflects the complex biological process underlying the healing process of a wound.

The validation study on an independent cohort further revealed the pivotal application of this genetic prognostic test in predicting the nature of wound healing. Using this cohort of chronic wound tissues with a single aetiology (venous ulcer) and in a double blinded test, the test clearly differentiated those wounds that healed from those that were non-healing (within 3 months). Collectively, it is concluded that the gene signature reported here provides vital information in predicting the clinical outcome of the nature of healing (to heal or to become chronic).

Thus, the clinical application is evident. A test using the signature on a given wound tissue would allow one immediately to distinguish the fate of the wound.

It has to be said that the signature is also highly able to distinguish acute wound tissue from normal tissue. The power to distinguish chronic wound tissue from normal tissue is significant, but nonetheless weaker than the acute-normal scenario. There are two important aspects to this information:

1. A chronic wound has mechanisms switched-off that gives the tissues a similar status in terms of the healing mechanism to normal skin or below that of normal skin. Whereas the acute wound has a clear driving mechanisms for the healing process. Therefore one of the powers within the signature is that it has deciphered the key mechanism underlying these process.
2. The tests on the cell models well mirrored the normal-acute-chronic situation, in that the 'acute' phase (within 2 hours after wounding) showed a dramatic change in its signature, compared with unwounded cells. On the other hand, in a 'healed' wound (after 4 hours), the signature appears similar to unwounded cell layer. Collectively, the signature provides some key molecular and cellular information with regard to the nature of the wound healing process.

In this study, we have adopted in vitro wound assays in order to evaluate if the changes in molecular signature seen in human wounds may be mirrored in vitro. We used two models to create cell wounds; to obtain the dynamics of the healing process. Using the ECIS model, both the ECIS trace and morphological observations have indicated that under the specified conditions, wound healing is at its linear phase between 0.5-3 hours after wounding. 4 hours after wounding, the wounds are virtually closed 'healed'. This is of course dependent upon the type of cells, i.e. endothelial cells and melanoma cells healed at a faster pace than keratinocytes. This is fully supported by the conventional scratch wounding assay (FIGS. 1 and 2). Using this cell model, we have shown that the signature seen in human wounds is mirrored in vitro.

In summary, the invention describes a new molecular signature that allows the classification and prognosis of the nature of human wounds: if a wound is to heal or to become chronic.

TABLE 1

The 25 gene signature list

| Molecule name | Change in human wounds |
|---|---|
| ARP2 | Decreased in chronic and increased in acute wounds |
| VEGF-D | Decreased in chronic and increased in acute wounds |
| IL17C | Decreased in chronic and increased in acute wounds |
| VEGF-C | Decreased in chronic wounds |
| beta-Catenin | Decreased in chronic wounds |
| RON | Decreased in chronic and increased in acute wounds |
| Endomucin-2 | Decreased in chronic wounds |
| IL22R | Increased in both acute and chronic wounds |
| WAVE2 | High in acute |
| IL8RB | Decreased in chronic and increased in acute wounds |
| Claudin-5 | Decreased in chronic and increased in acute wounds |
| TEM7R | Increased in both acute and chronic wounds |
| PTPRK | Increased in both acute and chronic wounds |
| BMP15 | Decreased in chronic wounds |
| PEDF | Decreased in human wounds |
| RhoGDI-G | Decreased in human wounds |
| N-WASP | Decreased in chronic and increased in acute wounds |
| AMFR | High in acute |
| Psoriasin | Increased in both acute and chronic wounds |
| Par4 | High in acute |
| TEM4 | High in acute |
| IL17BR | Decreased in chronic and increased in acute wounds |
| KAI1 | Increased in both acute and chronic wounds |
| CAR1 | Decreased in chronic and increased in acute wounds |
| CREBL1 | Decreased in chronic and increased in acute wounds |

TABLE 1b

Primers for the 25 gene signature list

| MOLECULE NAME | PRIMER PAIR (5'-'3) | |
|---|---|---|
| ARP2 | attgagcaagagcagaaact, and | (SEQ ID NO: 1) |
| | actgaacctgaccgtacattctggtgcttcaaatctct | (SEQ ID NO: 2) |
| VEGF-D | agatgaagaatggcaaagaa and | (SEQ ID NO: 3) |
| | actgaacctgaccgtacaatctgctgttcagatcgtt | (SEQ ID NO: 4) |
| IL17C | catctcaccctggagatacc, and | (SEQ ID NO: 5) |
| | actgaacctgaccgtacacatcgatacagcctctgc | (SEQ ID NO: 6) |
| VEGF-C | gctgctgcacattataacac and | (SEQ ID NO: 7) |
| | actgaacctgaccgtacaaactccttccccacatctat | (SEQ ID NO: 8) |
| β-Catenin | agggattttctcagtccttc, and | (SEQ ID NO: 9) |

TABLE 1b-continued

Primers for the 25 gene signature list

| MOLECULE NAME | PRIMER PAIR (5'-'3) |
|---|---|
| | actgaacctgaccgtacacatgccctcatctaatgtct (SEQ ID NO: 10) |
| RON | catccacccagtgccaac, (SEQ ID NO: 11) and |
| | actgaacctgaccgtacaccacacagtcagccacag (SEQ ID NO: 12) |
| Endomucin-2 | aaatgttgtcacaccaacaa, (SEQ ID NO: 13) and |
| | actgaacctgaccgtacaagctgttgacatcagagaca (SEQ ID NO: 14) |
| IL22R | agatgactgacaggttcagc, (SEQ ID NO: 15) and |
| | actgaacctgaccgtacagaatcgactctcactttggag (SEQ ID NO: 16) |
| WAVE2 | cagctgactacccaactctg, (SEQ ID NO: 17) and |
| | actgaacctgaccgtacaatctgcaccagtgaaagg (SEQ ID NO: 18) |
| IL8RB | tcaaattcatatgtctcagca, (SEQ ID NO: 19) and |
| | actgaacctgaccgtacagttgcccatgtcctcata, (SEQ ID NO: 20) |
| Claudin-5 | ttcctggaccacaactac, (SEQ ID NO: 21) and |
| | actgaacctgaccgtacacaccgagtcgtacactttgc (SEQ ID NO: 22) |
| TEM7R | cttgattggcagtatggagt, (SEQ ID NO: 23) and |
| | actgaacctgaccgtacagtctaccgccttgagaaag, (SEQ ID NO: 24) |
| PTPRK | tatggctgtacctccattgt, (SEQ ID NO: 25) and |
| | actgaacctgaccgtacaatatcgtagcatcccttcct (SEQ ID NO: 26) |
| BMP15 | gtgaagcccttgaccagt (SEQ ID NO: 27) and |
| | actgaacctgaccgtacattggtatagtcctcggtttg (SEQ ID NO: 28) |
| PEDF | ggtgctactcctctgcatt (SEQ ID NO: 29) and |
| | actgaacctgaccgtacaagaaaggatcctcctcctc (SEQ ID NO: 30) |
| RHOGDIG | agtcctcctggctgacaa (SEQ ID NO: 31) and |
| | actgaacctgaccgtacaaaagaagtggcaggaagagt, (SEQ ID NO: 32) |
| N-WASP | gagctggatgagaacaacac, (SEQ ID NO: 33) and |
| | actgaacctgaccgtacaaaagaagtggcaggaagagt, (SEQ ID NO: 34) |
| AMFR | cctacacagcggtcagatag, (SEQ ID NO: 35) and |
| | actgaacctgaccgtacaagcagaagtttctccctctt (SEQ ID NO: 36) |
| Psoriasin | aacttccccaacttccttag, (SEQ ID NO: 37) and |
| | actgaacctgaccgtacaagcaaggacagaaactcaga (SEQ ID NO: 38) |
| PAR4 | atgccaggagacgacctc (SEQ ID NO: 39) and |
| | actgaacctgaccgtacagatcttacgcttcccttacc (SEQ ID NO: 40) |
| TEM4 | gtctcgttcaagctggg (SEQ ID NO: 41) and |
| | actgaacctgaccgtacaggttgccgtgtcctcctc (SEQ ID NO: 42) |
| IL17BR | agtgactggggatagtgaag, (SEQ ID NO: 43) and |
| | actgaacctgaccgtacacagagcacaactgttccttt (SEQ ID NO: 44) |
| KAI1 | cattcgagactacaacagca ctgtactttgctttcctgct, (SEQ ID NO: 45) and |
| | ctgtagtcttcggaatggac' (SEQ ID NO: 46) |
| CAR1 | atggatctgaagaaattgga, (SEQ ID NO: 47) and |
| | actgaacctgaccgtacaagacaattttttgccactcat (SEQ ID NO: 48) |
| CREBL1 | ggggactatgaggagatgat, (SEQ ID NO: 49) and |
| | actgaacctgaccgtacagtggaggtcttgatgtgaat, (SEQ ID NO: 50) |

TABLE 2

The 14 gene refined signature list

ARP2
CREB11
VEGF-C
Psoriasin
IL22R
TEM4
IL8RB
IL17BR
Claudin-5
KAI1
PTPRK
CAR1
Endomuscin-2
TEM7R

TABLE 3

Prediction of wound healing using AO > 10

|   | 0  | 1 |
|---|----|---|
| 1 | 14 | 0 |
| 2 | 9  | 1 |
| 3 | 1  | 9 |

$X^2 = 25.33$,
p = 0.00000316,
Yate's p = 0.00003741
(note:
in vertical columns: 1 = chronic wound; 2 - normal skin, 3 = acute wound; in horizontal rows: 0, 1 are signature IDs

TABLE 4

Prediction of the healing wound using the AO123d three set format.

|   | 1  | 2 | 3 |
|---|----|---|---|
| 1 | 14 | 0 | 0 |
| 2 | 9  | 1 | 1 |
| 3 | 1  | 9 | 9 |

$X^2 = 25.868$,
p = 0.00003364,
Yate's p = 0.00054889
(note:
in vertical columns: 1 = chronic wound; 2 - normal skin, 3 = acute wound) In Horizontal rows: 1, 2, 3 are signature IDs)

TABLE 5

Distinguishing the chronic from acute using the refined F5 > 5 format

|   | 0  | 1 |
|---|----|---|
| 1 | 14 | 0 |
| 3 | 1  | 9 |

$X^2 = 20.26$,
p = 0.00000676,
Yate's p = 0.00004297
(note:
in vertical columns: 1 = chronic wound; 2 - normal skin, 3 = acute wound) In Horizontal rows: 0, 1 are signature IDs)

TABLE 6a

Distinguishing the acute from normal skin in two set format (6a-1left, F5-5) or three set format (right ao123) using the refined signature Table 6a1

|   | 0 | 1  |
|---|---|----|
| 2 | 8 | 2  |
| 3 | 0 | 10 |

$X^2 = 13.333$, p = 0.00026078, Yate's p = 0.00139833

Table 6a2

|   | 1 | 2 | 3 |
|---|---|---|---|
| 2 | 6 | 4 | 0 |
| 3 | 0 | 2 | 8 |

$X^2 = 14.667$, p = 0.00065328, Yate's p = 0.0053589
(note:
in vertical columns: 1 = chronic wound; 2 - normal skin, 3 = acute wound) In Horizontal rows: 0, 1 are signature IDs)

TABLE 6b

Distinguishing the chronic from normal skin in two set format (6b1, F2-8) or three set format (6b2 bd123) using the refined signature Table 6b1

|   | 0  | 1 |
|---|----|---|
| 1 | 14 | 0 |
| 2 | 7  | 3 |

$X^2 = 4.8$, p = 0.02846, Yate's p = 0.1176

Table 6b2

|   | 1  | 2 | 3 |
|---|----|---|---|
| 1 | 13 | 0 | 1 |
| 2 | 7  | 3 | 0 |

$X^2 = 5.280$, p = 0.07136, Yate's p = 0.3144
(note:
in vertical columns: 1 = chronic wound; 2 - normal skin, 3 = acute wound) In Horizontal rows: 0, 1, 2, 3 are signature IDs)

TABLE 7

Prediction of the healing wound using the full list of the signature All19

|   | 0  | 1 |
|---|----|---|
| 1 | 13 | 1 |
| 2 | 7  | 3 |
| 3 | 1  | 9 |

$X^2 = 17.365$, p = 0.00016953, Yate's p = 0.00101031
(note:
in vertical columns: 1 = chronic wound; 2 - normal skin, 3 = acute wound) In Horizontal rows: 0, 1 are signature IDs)

TABLE 8

Prediction of the healing wound using the full list of the signature All19abc

| | 1 | 2 | 3 |
|---|---|---|---|
| 1 | 13 | 0 | 1 |
| 2 | 7 | 1 | 2 |
| 3 | 1 | 0 | 9 |

$X^2 = 21.325$, $p = 0.00027298$, Yate's $p = 0.00415619$ (note:

in vertical columns: 1 = chronic wound; 2 - normal skin, 3 = acute wound) In Horizontal rows: 1, 2, 3 are signature IDs)

TABLE 9

Validation study using the refined signature kit on in vitro wound healing: the A431/H/M model.

| | low | Unchange | rise |
|---|---|---|---|
| Healed | 6 | 5 | 0 |
| Unwounded | 0 | 11 | 0 |
| 'acute' | 2 | 1 | 8 |

$X^2 = 31.941$ WITH D.F. = 4, $p = 0.00000374$

TABLE 10

Validation study using the refined signature kit on in vitro wound healing: the HaCaT model.

| | low | rise |
|---|---|---|
| Healed | 7 | 3 |
| Unwounded | 10 | 0 |
| 'acute' | 3 | 7 |

$X^2 = 11.1$ WITH D.F. = 2, $p = 0.003887$

TABLE 11

Validation study using the refined signature kit on in vitro wound healing: the HECV endothelial model (set-2).

| | low | rise |
|---|---|---|
| Healed | 8 | 4 |
| Unwounded | 12 | 0 |
| 'acute' | 1 | 11 |

$X^2 = 21.257$ WITH D.F. = 2, $p = 0.00002422$

TABLE 12

Validation study using the refined signature kit on in vitro wound healing: the HECV-fibroblast model (set-2).

| | low | rise |
|---|---|---|
| Healed | 7 | 3 |
| Unwounded | 10 | 0 |
| 'acute' | 9 | 1 |

$X^2 = 17.5$ WITH D.F. = 2, $p = 0.0001584$

APPENDIX-1

List of gene transcript tested, name, and accession number

| Name | Accession number |
|---|---|
| Cyr61 | AF307860 |
| CCN2 | NM_001901 |
| CCN3 | NM_002514 |
| Actin | NM_001101 |
| GAPDH | NM_002046 |
| ARP2 | AF006082 |
| TEM4 | AF378754 |
| IL8RB | NM_001557 |
| TEM8 | NM_032208 |
| TEM7R | AF378757 |
| WAVE1 | AF134303 |
| WAVE2 | AB026542 |
| NOTICH1 | AF308602 |
| AMFR | L35233 |
| IL8R | U58828 |
| CMG2 | AY040326 |
| IL17A | NM_002190 |
| PAR4 | AB108448 |
| IL17B | NM_014443 |
| BMP7 | BC004248 |
| CD24 | BC064619 |
| PlGF1 | X54936 |
| Chordinv2 | AF209930 |
| VEGF-D | D89630 |
| IL17BR | AF212365 |
| VEGF-R | E13256 |
| N-WASP | D88460 |
| HGFL | NM_020998 |
| RGMa | NM_020211 |
| VEGF-R2 | AF063658 |
| RGMc | BC085604 |
| IL13 | U70981 |
| BMP15 | NM_005448 |
| Kiss1R | NM_032551 |
| LYN | BC068551 |
| L1CAM | M77640 |
| VEGF | E14233 |
| CD49F | NM_002203 |
| RON | NM_002447 |
| Claudin-5 | NM_003277 |
| BMP9 | AF188285 |
| CD34 | M81104 X60172 |
| CMG1 | AY040325 |
| KAI1 | U20770 |
| OSP-C | NM_001040060 |
| SATB1 | NM_002971 |
| COM1 | NM_012385 |
| IL17C | NM_013278 |
| TEM1 | XM_006495 |
| IL4 | M13982 |
| OSPA | NM_001040058 |
| WAVE3 | AB026543 |
| TEM6 | AF378756 |
| PEDF | M76979 |
| BMP8 | NM_181809 |
| RHO GDI-G | AF498928 |
| JAK1 | M64174 M35203 |
| AAMP | M95627 |
| SSTR1 | L14865 |
| SATB2 | NM_015265 |
| GDF9A | NM_005260 |
| SHH | L38518 |
| BMP10 | NM_014482 |
| CAR1 | NM_001338 |
| SDF1 | XM_165565 |
| PTPRK | AF533875 |
| ROCK1 | D87931 |
| EHM2 | AB032179 |
| IL24 | BC009681 |
| KISS1 | AY117143 |
| VEGF-C | AF244813 |
| Chordin V1 | AF209929 |
| STYK1 | NM_018423 |
| Chordin V3 | AF283325 |

| Name | Accession number |
|---|---|
| Psoriasin | M86757 |
| β-Catenin | P35222 |
| Endomuscin-2 | AB034695 |
| SNAIL | AF131208 |
| RHO-C | L25081 |
| CREB11 | NM_004381 |

| Name | Accession number |
|---|---|
| RHO-8 | AF498969 |
| IL22R | BC029273 |
| FAP | U09278 |
| DRIM | NM_014503 |

The invention claimed is:

1. A method for identifying chronic mammalian wound tissue or for determining the prognosis of mammalian wound tissue, which method comprises:
   (a) examining a sample of wound tissue from an individual to determine the levels of expression of genes encoding molecular markers selected from the set of molecular markers consisting of:
   ARP2, CREBL1, VEGF-C, Psoriasin, IL22R, TEM4, IL8RB, IL17BR, Claudin-5, KaI1, PTPRK, CAR1, Endomuscin-2, and TEM7R;
      wherein the step of determining the level of expression of genes is determined by PCR using the molecular marker primer sets:
   Psoriasin: SEQ ID NO: 37, SEQ ID NO: 38;
   Claudin-5: SEQ ID NO: 21, SEQ ID NO: 22;
   IL8RB: SEQ ID NO: 19, SEQ ID NO: 20;
   IL22R: SEQ ID NO: 15, SEQ ID NO: 16;
   PTPRK: SEQ ID NO: 25, SEQ ID NO: 26;
   TEM4: SEQ ID NO: 41, SEQ ID NO: 42;
   TEM7R: SEQ ID NO: 23, SEQ ID NO: 24;
   VEGF-C: SEQ ID NO: 7, SEQ ID NO: 8;
   ARP2: SEQ ID NO: 1, SEQ ID NO: 2;
   CAR1: SEQ ID NO: 47, SEQ ID NO: 48;
   Endomucin: SEQ ID NO: 13, SEQ ID NO: 14;
   IL7BR: SEQ ID NO: 43, SEQ ID NO: 44;
   KaI1: SEQ ID NO: 45, SEQ ID NO: 46; and
   CREBL1: SEQ ID NO: 49, SEQ ID NO: 50; and
   further wherein the wound tissue is from a chronic wound when:
   (b) the following genes show decreased expression relative to control tissue:
   ARP2, CREB1l, VEGF-C, IL8RB, IL17BR, Claudin-5, CAR1 and Endomuscin-2, and;
   (c) TEM 4 shows normal expression relative to control tissue; and
   (d) the following genes show increased expression relative to control tissue:
   Psoriasin, IL22R, KAI1, PTPRK, and TEM7R.

2. The method according to claim 1 wherein additional studies are undertaken to determine whether any one or more of the following markers show a decreased level of expression indicative of chronic wound tissue relative to control tissue:
   VEGF-D, IL17C, β-Catenin, RON, BMP15, PEDF, RhoGDI-G and N-WASP and;
   any one or more of the following markers show a normal level of expression indicative of chronic wound tissue relative to control tissue:
   WAVE2, AMFR, PAR4;
      wherein the step of determining the level of expression of markers is determined by PCR using the molecular marker primer sets:
   VEGF-D: SEQ ID NO: 3, SEQ ID NO: 4;
   IL17C: SEQ ID NO: 5, SEQ ID NO: 6;
   β-Catenin: SEQ ID NO: 9, SEQ ID NO: 10;
   RON: SEQ ID NO: 11, SEQ ID NO: 12;
   BMP15: SEQ ID NO: 27, SEQ ID NO: 28;
   PEDF: SEQ ID NO: 29, SEQ ID NO: 30;

RhoGDI-G: SEQ ID NO: 31, SEQ ID NO: 32;
N-WASP: SEQ ID NO: 33, SEQ ID NO: 34;
WAVE2: SEQ ID NO: 17, SEQ ID NO: 18;
AMFR: SEQ ID NO: 35, SEQ ID NO: 36; and
PAR4: SEQ ID NO: 39, SEQ ID NO: 40.

3. The method according to claim 1 wherein the method also involves identifying acute mammalian wound tissue, using a method which comprises:
 (a) examining a sample of wound tissue from the individual in order to determine the levels of expression of genes encoding the following molecular markers ARP2, CREBL1, VEGF-C, Psoriasin, IL22R, TEM4, IL8RB, IL17BR, Claudin-5, KaI1, PTPRK, CAR1, Endomucin-2, TEM7R, and;
 (b) where the individual from whom the tissue sample has been taken has an acute wound when the following genes or markers show increased expression relative to control tissue: ARP2, CREBL1, Psoriasin, IL22R, TEM4, IL8RB, IL17BR, Claudin-5, KaI1, PTPRK, CAR1 and TEM7R.

4. The method according to claim 3 wherein the individual from whom the sample has been taken has an acute wound when the molecular markers VEGF-C and Endomucin-2 show normal expression relative to control tissue.

5. The method according to claim 3 wherein the individual from whom the sample has been taken has an acute wound when any one or more of the following markers show an increased level of expression relative to control tissue:
 VEGF-D, IL17C, RON, WAVE2, N-WASP AMFR, and PAR4 and;
 any one or more of the following markers show a normal level of expression relative to control tissue:
 β-Catenin, BMP15 and;
 any one or more of the following markers show a decreased level of expression relative to control tissue:
 PEDF, RhoGDI-G.

6. The method according to claim 1 wherein said tissue is human tissue.

7. The method according to claim 1 wherein the levels of expression of genes are determined by measuring RNA.

8. The method according to claim 7 wherein said RNA is mRNA.

9. The method of claim 1 wherein the levels of expression of genes are determined by measuring the corresponding encoded proteins.

10. The method according to claim 9 wherein the proteins are measured using antibodies.

11. The method according to claim 10 wherein said antibodies are monoclonal.

12. The method according to claim 10 wherein said antibodies are labelled with a tag whereby the existence of bound antibody to target protein can be determined.

13. The method according to claim 1 wherein the levels of expression of genes are determined relative to a reference gene.

14. The method according to claim 13 wherein said reference gene is a gene expressed within a control sample of tissue.

15. The method according to claim 14 wherein said control sample is normal skin tissue.

16. The method according to claim 15 wherein said normal skin tissue is taken from the same limb or region as said sample of wound tissue.

17. The method according to claim 13 wherein said reference gene is a housekeeping gene.

18. The method according to claim 17 wherein said reference gene is GAPDH.

19. The method according to claim 13 wherein said reference gene is a recognised standard for expression of one or more of said genes in a healthy individual.

20. A kit comprising:
 (a) a plurality of probes for detecting and quantifying the expression level of all of the following molecular markers ARP2, CREBL1, VEGF-C, Psoriasin, IL22R, TEM4, IL8RB, IL17BR, Claudin-5, KaI1, PTPRK, CAR1, Endomucin-2, and TEM7R; and
 (b) optionally, reagents and instructions pertaining to the use of said probes;
  wherein the probes comprise primer sequences selected from the group consisting of:
 Psoriasin: SEQ ID NO: 37, SEQ ID NO: 38;
 Claudin-5: SEQ ID NO: 21, SEQ ID NO: 22;
 IL8RB: SEQ ID NO: 19, SEQ ID NO: 20;
 IL22R: SEQ ID NO: 15, SEQ ID NO: 16;
 PTPRK: SEQ ID NO: 25, SEQ ID NO: 26;
 TEM4: SEQ ID NO: 41, SEQ ID NO: 42;
 TEM7R: SEQ ID NO: 23, SEQ ID NO: 24;
 VEGF-C: SEQ ID NO: 7, SEQ ID NO: 8;
 ARP2: SEQ ID NO: 1, SEQ ID NO: 2;
 CAR1: SEQ ID NO: 47, SEQ ID NO: 48;
 Endomucin: SEQ ID NO: 13, SEQ ID NO: 14;
 IL7BR: SEQ ID NO: 43, SEQ ID NO: 44;
 KaI1: SEQ ID NO: 45, SEQ ID NO: 46; and
 CREBL1: SEQ ID NO: 49, SEQ ID NO: 50.

21. The kit according to claim 20 wherein said kit additionally comprises:
 (a) at least one probe limited to that/those for identifying and quantifying the expression level of at least one transcript or polypeptide/protein of at least one of the following genes VEGF-D, IL17C, beta-Catenin, RON, WAVE2, BMP15, PEDF, RhoGDI-G, N-WASP, Par4 and AMFR, and;
 (b) optionally, reagents and instructions pertaining to the use of said probes which instructions describe how to determine the expression level of each of said genes;
  wherein the probes comprise primer sequences selected from the group consisting of:
 VEGF-D: SEQ ID NO: 3, SEQ ID NO: 4;
 IL17C: SEQ ID NO: 5, SEQ ID NO: 6;
 β-Catenin: SEQ ID NO: 9, SEQ ID NO: 10;
 RON: SEQ ID NO: 11, SEQ ID NO: 12;
 BMP15: SEQ ID NO: 27, SEQ ID NO: 28;
 PEDF: SEQ ID NO: 29, SEQ ID NO: 30;
 RhoGDI-G: SEQ ID NO: 31, SEQ ID NO: 32;
 N-WASP: SEQ ID NO: 33, SEQ ID NO: 34;
 WAVE2: SEQ ID NO: 17, SEQ ID NO: 18;
 AMFR: SEQ ID NO: 35, SEQ ID NO: 36; and
 PAR4: SEQ ID NO: 39, SEQ ID NO: 40.

22. A microarray comprising or containing any one or more of the aforementioned sets of probes of claim 20 for identifying the expression of any one or more of the molecular markers.

23. A kit for determining wound type in a patient, which kit comprises:
 (a) at least one microarray comprising a plurality of probes limited to those for identifying at least one set of the molecular markers described in the methods according to claims 1-19; and, optionally,
 (b) a second microarray comprising a plurality of probes limited to those for identifying the same set of molecular markers in an internal standard that represents the normal level of expression of said markers;

wherein the probes comprise primer sequences selected from the group consisting of:

Psoriasin: SEQ ID NO: 37, SEQ ID NO: 38;
Claudin-5: SEQ ID NO: 21, SEQ ID NO: 22;
IL8RB: SEQ ID NO: 19, SEQ ID NO: 20;
IL22R: SEQ ID NO: 15, SEQ ID NO: 16;
PTPRK: SEQ ID NO: 25, SEQ ID NO: 26;
TEM4: SEQ ID NO: 41, SEQ ID NO: 42;
TEM7R: SEQ ID NO: 23, SEQ ID NO: 24;
VEGF-C: SEQ ID NO: 7, SEQ ID NO: 8;
ARP2: SEQ ID NO: 1, SEQ ID NO: 2;
CAR1: SEQ ID NO: 47, SEQ ID NO: 48;
Endomucin: SEQ ID NO: 13, SEQ ID NO: 14;
IL7BR: SEQ ID NO: 43, SEQ ID NO: 44;
KaI1: SEQ ID NO: 45, SEQ ID NO: 46;
CREBL1: SEQ ID NO: 49, SEQ ID NO: 50;
VEGF-D: SEQ ID NO: 3, SEQ ID NO: 4;
IL17C: SEQ ID NO: 5, SEQ ID NO: 6;
β-Catenin: SEQ ID NO: 9, SEQ ID NO: 10;
RON: SEQ ID NO: 11, SEQ ID NO: 12;
BMP15: SEQ ID NO: 27, SEQ ID NO: 28;
PEDF: SEQ ID NO: 29, SEQ ID NO: 30;
RhoGDI-G: SEQ ID NO: 31, SEQ ID NO: 32;
N-WASP: SEQ ID NO: 33, SEQ ID NO: 34;
WAVE2: SEQ ID NO: 17, SEQ ID NO: 18;
AMFR: SEQ ID NO: 35, SEQ ID NO: 36; and
PAR4: SEQ ID NO: 39, SEQ ID NO: 40.

* * * * *